US006235882B1

(12) United States Patent
Chen (10) Patent No.: US 6,235,882 B1
(45) Date of Patent: May 22, 2001

(54) GENE ENCODING A PUTATIVE EFFLUX PROTEIN FOR SOLVENTS/ANTIBIOTICS IN PSEUDOMONAS MENDOCINA

(75) Inventor: Kevin Keqin Chen, Beijing (CN)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/333,254

(22) Filed: Jun. 15, 1999

Related U.S. Application Data (60) Division of application No. 09/183,270, filed on Oct. 30, 1998, which is a continuation-in-part of application No. 08/961,738, filed on Oct. 31, 1997, now abandoned.

(51) Int. Cl.[7] ............................... C07K 1/00; C07H 21/02
(52) U.S. Cl. ......................................... 530/350; 536/23.1
(58) Field of Search .......................... 530/350; 536/23.1; 436/94

(56) References Cited

U.S. PATENT DOCUMENTS

| 4,657,863 | 4/1987 | Maxwell et al. ...................... 435/142 |
| 4,968,612 | 11/1990 | Hsieh .................................... 435/142 |

FOREIGN PATENT DOCUMENTS

| 05328980 | 12/1993 | (JP) . |
| 05328981 | 12/1993 | (JP) . |
| 05336979 | 12/1993 | (JP) . |

OTHER PUBLICATIONS

Asako, H. et al., *Applied and Environmental Microbiology*, 63, No 4, 1428–1433, 1997.
Aono R. et al., *Applied and Environmental Microbiology*, 60, No. 12, 4624–4626, 1994.
Paulsen, I. et al., *Microbiological Reviews*, 60, No. 4, 575–608, 1996.
Wright et al., *Appln. Environ. Microbiol.*, 60, 235–242, 1994.
Duetz et al., *Appln. Environ. Microbiol.*, 60, 2858–2863, 1994.
Leahy et al., *Appl. Environ. Microbiol.*, 62, 825–833, 1996.
Li et al., *J. Bacteriol.*, 180, 2987–2991, 1998.
Ramos et al., *J. Bacteriol.*, 180, 3323–3329, 1998.
Hardwood, C. et al., *Journal of Bacteriology*, 176, No. 21, 6479–6488, 1994.
Nikaido H., *Journal of Bacteriology*, 178, No. 20, 5853–5859, 1996.
Isken S. et al., *Journal of Bacteriology*, 178, No. 20, 6056–6058, 1996.

Primary Examiner—Christopher S. F. Low
Assistant Examiner—Devesh Srivastava
(74) Attorney, Agent, or Firm—Inna Y. Belopolsky (57) ABSTRACT

This invention relates to the isolation of a novel putative efflux gene from *Pseudomonas mendocina*. The putative efflux gene is useful for probing an organism's efflux system to gain an understanding of the mechanisms of solvent tolerance. The invention further provides a *Pseudomonas mendocina* strain deficient in this gene. This strain is unable to grow in the presence of chloramphenicol and, compared to the wildtype strain, grows slowly in the presence of high concentrations of PHBA.

2 Claims, 2 Drawing Sheets

SEQUENCE LISTING

<160> NUMBER OF SEQ ID NOS: 6

<210> SEQ ID NO: 1
<211> LENGTH: 1249
<212> TYPE: DNA
<213> ORGANISM: Pseudomonas mendocina KR-1

<400> SEQUENCE: 1

```
atgctcagta gagtcgggtg gctgcagggc agtcatggcc acccgtgcat ccggggatc     60
gaggtcgggc cagccagggc gagccggctt cgccgcttgc ctgcacgaag gatgctccgt    120
tgtttgcgcg ccccatacac cgacgtgctg tcgtcaacgc caacagttca tgaggaactc    180
gccatgcgct tgaatgttgc ggttgtagtt ttgctgaccg gcctggtggc ggcgacctac    240
ggcttcggga tctatctgtt cgcccagctc gtacccgata tgcaggcgtc cctgggttc     300
ggtttttcct acgtgggcac catcaccgct tcagcgcaac tggggttcct gctctgcgcc    360
atgctggcgg tctggctgac gcccaaggtc ggcggcggca ggatgatcgc ggcgtcgggg    420
gcggtgtgcg cgctggcgtt gctgctgatc ccgctgtcga gcaacacatt cgtcataggt    480
gtgctgctga ccctgctggc gggcaccgcc gccactgtct tcgtgcccat ggtcgatgtc    540
atcgccaggg tggtcgccta ccgctaccga ggcttggcca tggggctggt gtccagcggg    600
accagctatg gcgtcgccat caacagtctg ctggtgccca tctatgcccc caggcgag     660
tggcgcagcg tctggtgggt ggtggggctg ctcacgttgg cgatgaccgt gctggtgctg    720
gtggtgctca gcggggagg cttgcttggc caggccctgc cgtcagcgcc gacggcaacg    780
acagacgaag ccgcctcatc cagcgggctc tcaggactga taagacctg ggtactgctg     840
atctggtcaa tgaacttcct gataggtttc gccaccttcc cgttccagac ctacctctcg    900
tcctatctcc gcaccgagct tggcttcgac gtgcagtaca ccgcccaggt ctgggccgtg    960
atcggattcg tcggcatgtt cgccgggctc gcggtcggct ggctctcgga ccggaccggt   1020
ttgcgctttg ccatgtatct cgtctacggc tgcgtggtga cggcggcgct gatcttcgtg   1080
gtgcagcctt caggtcattg gcccctggtt gccgccgtgc tgttttccac tgccttctat   1140
cccatcttcg gccttattcc ggcttacgtt tccaagttgg catcctccag cgccatggcc   1200
gtctcgatct tcggtatcgc caatgtgatg caaggctccg gcggcatgc               1249
```

<210> SEQ ID NO: 2
<211> LENGTH: 416
<212> TYPE: PRT
<213> ORGANISM: Pseudomonas mendocina KR-1

<400> SEQUENCE: 2

```
Met Leu Ser Arg Val Gly Trp Leu Gln Gly Ser His Gly His Pro Cys
  1               5                  10                  15

Ile Arg Gly Ile Glu Val Gly Pro Ala Arg Ala Ser Arg Leu Arg Arg
             20                  25                  30

Leu Pro Ala Arg Arg Met Leu Arg Cys Leu Arg Ala Pro Tyr Thr Asp
         35                  40                  45

Val Leu Ser Ser Thr Pro Thr Val His Glu Glu Leu Ala Met Arg Leu
     50                  55                  60

Asn Val Ala Val Val Val Leu Leu Thr Gly Leu Val Ala Ala Thr Tyr
 65                  70                  75                  80

Gly Phe Gly Ile Tyr Leu Phe Ala Gln Leu Val Pro Asp Met Gln Ala
                 85                  90                  95
```

-continued

```
Ser Leu Gly Phe Gly Phe Ser Tyr Val Gly Thr Ile Thr Ala Ser Ala
            100                 105                 110

Gln Leu Gly Phe Leu Leu Cys Ala Met Leu Ala Val Trp Leu Thr Pro
        115                 120                 125

Lys Val Gly Gly Arg Met Ile Ala Ala Ser Gly Ala Val Cys Ala
130                 135                 140

Leu Ala Leu Leu Ile Pro Leu Ser Ser Asn Thr Phe Val Ile Gly
145                 150                 155                 160

Val Leu Leu Thr Leu Leu Ala Gly Thr Ala Ala Thr Val Phe Val Pro
                165                 170                 175

Met Val Asp Val Ile Ala Arg Val Val Ala Tyr Arg Tyr Arg Gly Leu
                180                 185                 190

Ala Met Gly Leu Val Ser Ser Gly Thr Ser Tyr Gly Val Ala Ile Asn
            195                 200                 205

Ser Leu Leu Val Pro Ile Tyr Ala Pro Gln Gly Glu Trp Arg Ser Val
        210                 215                 220

Trp Trp Val Val Gly Leu Leu Thr Leu Ala Met Thr Val Leu Val Leu
225                 230                 235                 240

Val Val Leu Lys Arg Gly Gly Leu Leu Gly Gln Ala Leu Pro Ser Ala
                245                 250                 255

Pro Thr Ala Thr Thr Asp Glu Ala Ala Ser Ser Ser Gly Leu Ser Gly
                260                 265                 270

Leu Ile Arg Pro Trp Val Leu Leu Ile Trp Ser Met Asn Phe Leu Ile
            275                 280                 285

Gly Phe Ala Thr Phe Pro Phe Gln Thr Tyr Leu Ser Ser Tyr Leu Arg
        290                 295                 300

Thr Glu Leu Gly Phe Asp Val Gln Tyr Thr Ala Gln Val Trp Ala Val
305                 310                 315                 320

Ile Gly Phe Val Gly Met Phe Ala Gly Leu Ala Val Gly Trp Leu Ser
                325                 330                 335

Asp Arg Thr Gly Leu Arg Phe Ala Met Tyr Leu Val Tyr Gly Cys Val
                340                 345                 350

Val Thr Ala Ala Leu Ile Phe Val Val Gln Pro Ser Gly His Trp Pro
            355                 360                 365

Leu Val Ala Ala Val Leu Phe Ser Thr Ala Phe Tyr Pro Ile Phe Gly
        370                 375                 380

Leu Ile Pro Ala Tyr Val Ser Lys Leu Ala Ser Ser Ala Met Ala
385                 390                 395                 400

Val Ser Ile Phe Gly Ile Ala Asn Val Met Gln Gly Ser Gly Gly Met
                405                 410                 415
```

<210> SEQ ID NO: 3
<211> LENGTH: 26
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: primer

<400> SEQUENCE: 3
atgctcagta gagtcgggtg gctgca                                    26

<210> SEQ ID NO: 4
<211> LENGTH: 24
<212> TYPE: DNA

-continued

```
<213> ORGANISM: Artificial Sequence
<220> FEATURE:
<223> OTHER INFORMATION: Description of Artificial Sequence: primer
<220> FEATURE:
<223> OTHER INFORMATION: primer

<400> SEQUENCE: 4
ttacgccaag cttgcatgcc gccg                                          24

<210> SEQ ID NO: 5
<211> LENGTH: 23
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: unsure
<222> LOCATION: (9)
<223> OTHER INFORMATION: n = g, a, c or t(u)
<220> FEATURE:
<221> NAME/KEY: unsure
<222> LOCATION: (15)
<223> OTHER INFORMATION: n = g, a, c or t(u)
<220> FEATURE:
<221> NAME/KEY: unsure
<222> LOCATION: (18)
<223> OTHER INFORMATION: n = g, a, c or t(u)
<220> FEATURE:
<221> NAME/KEY: unsure
<222> LOCATION: (21)
<223> OTHER INFORMATION: n = g, a, c or t(u)

<400> SEQUENCE: 5
carttrctnc ayaangtngg nat                                           23

<210> SEQ ID NO: 6
<211> LENGTH: 21
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: unsure
<222> LOCATION: (7)
<223> OTHER INFORMATION: n = g, a, c or t(u)
<220> FEATURE:
<221> NAME/KEY: unsure
<222> LOCATION: (19)
<223> OTHER INFORMATION: n = g, a, c or t(u)

<400> SEQUENCE: 6
ctaytcnaty tcytcrtanr g                                             21
```

GENE ENCODING A PUTATIVE EFFLUX PROTEIN FOR SOLVENTS/ANTIBIOTICS IN PSEUDOMONAS MENDOCINA

This is a division of application Ser. No. 09/183,270 filed Oct. 30, 1998 now pending.

This application is a continuation-in-part application of U.S. application Ser. No. 08/961,738, filed Oct. 31, 1997, and now abandoned.

FIELD OF INVENTION

The present invention relates to the fields of molecular biology and microbiology. More specifically, this invention pertains to a novel gene encoding a putative efflux protein for solvents/antibiotics in Pseudomonas mendocina.

BACKGROUND

Toxicity of aromatic solvents to microorganisms presents a major problem to work in the field of microbiology. Varied and poorly understood factors appear to influence solvent tolerance. Increasingly, attention has turned to genetic manipulation to create microbes that thrive in high concentrations of organic solvents. Understanding the mechanisms of solvent tolerance can be exploited in the future to generate microbes with enhanced biocatalytic potential.

One enzymatic pathway of increasing commercial interest controls toluene degradation. The first enzyme in the toluene degradation (TMO) pathway is toluene-4-monooxygenase (TMO; EC 1.14.13 and EC 1.18.1.3). Bacteria that possess the TMO pathway are useful for the degradation of toluene and other organics and are able to use these as their sole source of carbon (Wright et al., Appl. Environ. Microbiol. 60:235–242 (1994); Duetz et al., Appl. Environ. Microbiol. 60:2858–2863 (1994); Leahy et al., Appl. Environ. Microbiol. 62:825–833 (1996)). Bacteria that possess the TMO pathway are primarily restricted to the genus Pseudomonas. Pseudomonas putida, Pseudomonas fluorescens, Pseudomonas aeruginosa and Pseudomonas mendocina are the most commonly utilized species.

Recently, various strains of Pseudomonas possessing the TMO pathway have been used to produce muconic acid from toluene via manipulation of growth conditions U.S. Pat. No. 4,657,863; U.S. Pat. No. 4,968,612). Additionally, strains of Enterobacter with the ability to convert p-cresol to p-hydroxybenzoic acid (PHBA) have been isolated from soil (JP 05328981). Further, JP 05336980 and JP 05336979 disclose isolated strains of Pseudomonas putida with the ability to produce PHBA from p-cresol.

Although the above cited methods are useful for the production of PHBA, these methods are limited by the high cost and toxicity of the aromatic substrate, p-cresol. Furthermore, the above methods use an isolated wildtype organism that converts part of the p-cresol to PHBA while the remainder is further metabolized. The utility of these methods is limited by low yields and an inability to control further degradation of the desired product.

Previous studies indicated that cell growth and the activity of the enzymes in the metabolic toluene degradation pathway were inhibited in the presence of high concentrations of PHBA. Therefore, one problem to overcome is to develop a method of improving cell tolerance to high levels of PHBA or other aromatic solvents. During evolution, bacteria have developed a number of mechanisms which help to protect them from environmental toxins and various antibiotics. (Asako et al., Appl. Environ. Microbiol. 63:1428–1433 (1997); Aono et al., Appl. Environ. Microbiol. 60:4624–4626 (1994)). Many cytoplasmic membrane transport systems have been demonstrated to play an important role in bacteria by conferring resistance to toxic compounds. One of the most widespread is the active efflux of the toxic compounds from cells (Paulsen. et al., Microbiol. Rev. 60:575–608 (1996)).

Overexpression of an efflux system or its expression from a plasmid vector results in increased resistance of bacteria to a variety of toxic substances, while inactivation of an efflux system causes an increase in sensitivity to antibiotics and toxic substances (Li et al., J Bacteriol. 180:2987–2991 (1998); Ramos. et al., J Bacteriol. 180:3323–3329 (1998)). Such efflux systems are increasingly being recognized in a wide range of bacteria. Comparative amino acid sequence analysis of various transport proteins plus function assays has enabled the identification of a number of distinct families and super-families of transports.

SUMMARY OF THE INVENTION

The present invention provides a gene encoding a putative efflux protein for solvents or antibiotics in Pseudomonas mendocina. The invention further provides a Pseudomonas mendocina strain deficient in this gene that is unable to grow in the presence of chloramphenicol and, compared to the wildtype strain, grows slowly in the presence of high concentrations of PHBA.

Figure 2:
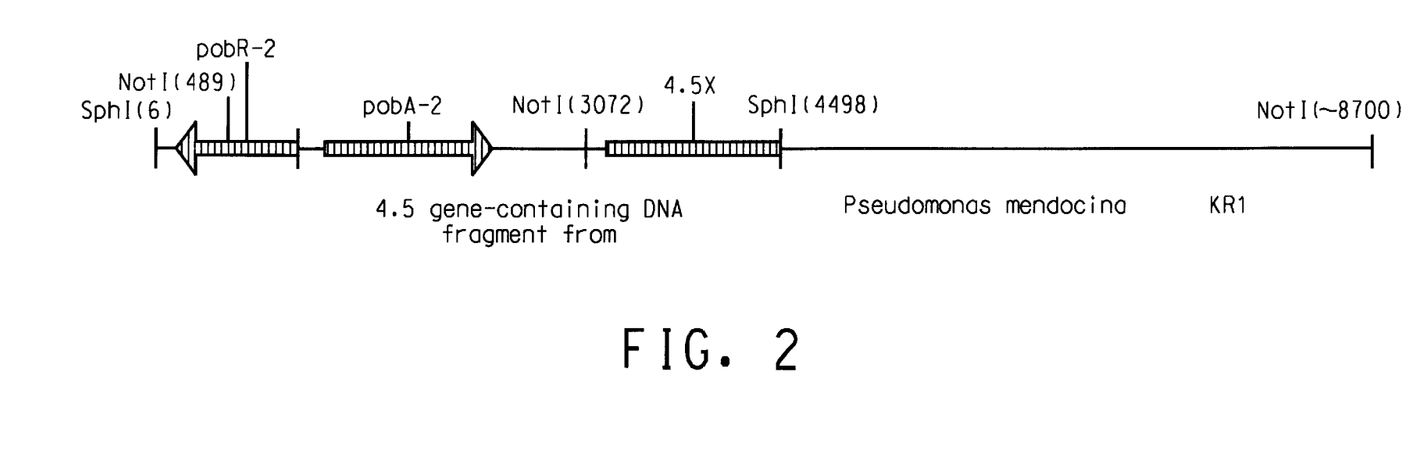
FIG. 2 schematically represents the 4.5x gene-containing DNA molecule from *Psuedomonas mendocina*-KR-1.

The instant invention relates to isolated nucleic acid molecules encoding all or a substantial portion of a putative efflux protein. The isolated nucleic acid molecule encoding a putative efflux protein is selected from the group consisting of (a) an isolated nucleic acid molecule encoding all or a substantial portion of the amino acid sequence set forth in SEQ ID NO:2; (b) an isolated nucleic acid molecule that hybridizes with the isolated nucleic acid molecule of (a) under the following hybridization conditions: 0.1×SSC, 0.1% SDS at 65° C.; and (c) an isolated nucleic acid molecule that is complementary to (a) or (b). The nucleic acid molecules and corresponding polypeptides are contained in the accompanying Sequence Listing and described in the Brief Description of the Invention and the FIG. 2. More particularly, the invention is a 5.8 kb NotI nucleic acid molecule isolated from Psuedomonas mendocina KR-1 encoding a putative 4.5x gene and the accessory nucleic acid molecules for the expression of the gene as characterized by the restriction map of FIG. 2.

In another embodiment, the instant invention relates to chimeric genes encoding a putative efflux protein or to chimeric genes that comprise nucleic acid molecules as described above, the chimeric genes operably linked to suitable regulatory sequences, wherein expression of the chimeric genes results in altered levels of the encoded proteins in transformed host cells.

In a further embodiment, the instant invention concerns a recombinant host cell comprising in its genome a chimeric gene encoding a putative efflux protein as described above, operably linked to at least one suitable regulatory sequence, wherein expression of the chimeric gene results in production of altered levels of the putative efflux protein in the transformed host cell. The transformed host cells can be of eukaryotic or prokaryotic origin. A preferred embodiment uses E. coli as the host bacterium.

In an alternate embodiment, the present invention provides methods of obtaining a nucleic acid molecule encoding all or substantially all of the amino acid sequence encoding a putative efflux protein comprising either hybridization or primer-directed amplification methods known in the art and using the above described nucleic acid molecules. A primer-amplification-based method uses SEQ ID NO:1. The product of these methods is also part of the invention.

The invention further provides a method for the production of increased levels of PHBA comprising: (i) culturing a Pseudomonas strain in a medium containing an aromatic organic substrate, at least one suitable carbon source, and a nitrogen source, wherein the Pseudomonas strain comprises altered levels of a gene encoding a putative efflux protein, whereby PHBA accumulates; and (ii) recovering the PHBA.

BRIEF DESCRIPTION OF THE DRAWINGS AND SEQUENCE DESCRIPTIONS

The invention can be more fully understood from the following detailed description and the accompanying sequence descriptions which form a part of this application.

The following sequence descriptions and sequences listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (2):345–373 (1984) which are herein incorporated by reference. The symbols and format used for nucleotide and amino acid sequence data comply with the rules set forth in 37 C.F.R. §1.822.

SEQ ID NO:1 is the the nucleotide sequence of the putative efflux 4.5x gene isolated from *Pseudomonas mendocina* KR-1.

SEQ ID NO:2 is the deduced amino acid sequence of the nucleotide sequence comprising the putative efflux 4.5x gene isolated from *Pseudomonas mendocina* KR-1.

SEQ ID NO:3 is the nucleotide sequence of the 5' primer used to detect the disruption of the putative efflux 4.5x gene.

SEQ ID NO:4 is the nucleotide sequence of the 3' primer used to detect the disruption of the putative efflux 4.5x gene.

SEQ ID NO:5 is the nucleotide sequence of the 5' primer used to generate 1.2-kb pobA gene molecule.

SEQ ID NO:6 is the the nucleotide sequence of the 3'primer used to generate 1.2-kb pobA gene fragment.

DETAILED DESCRIPTION OF THE INVENTION

A putative efflux 4.5x gene has been isolated that is located immediately downstream of the pobA gene in *Pseudomonas mendocina*. Efflux proteins play an important role in bacteria by conferring resistance to toxic compounds such as aromatic solvents. Over expressing an efflux system or its expression from a plasmid vector increases resistance of bacteria to a variety of toxic substances, while inactivating an efflux system increases sensitivity to antibiotics and toxic substances. Applicants have also provided a mutant of *Pseudomonas mendocina* containing a disrupted putative efflux 4.5x gene. The mutant has a different phenotype of solvent/antibiotic resistance compared with wildtype *Pseudomonas mendocina*.

In the context of this disclosure, a number of terms shall be utilized. "PHBA" is the abbreviation for p-hydroxybenzoic acid which is also known as p-hydroxybenzoate.

The term "Kam" refers to a gene encoding Kanamycin resistance.

The term "Amp" refers to a gene encoding Ampicillin resistance.

The term "Strep" refers to a gene encoding Streptomycin resistance.

The term "Tet" refers to a gene encoding tetracycline resistance.

The term "CM" refers to choromphenecol.

"PCR" is the abbreviation for polymerase chain reaction.

The term "pobA" refers to a gene encoding the p-hydroxybenzoate hydroxylase enzyme.

An "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

"Substantially similar" refers to nucleic acid molecules wherein changes in one or more nucleotide bases result in substitution of one or more amino acids, but do not affect the functional properties of the protein encoded by the DNA sequence. "Substantially similar" also refers to nucleic acid molecules wherein changes in one or more nucleotide bases do not affect the ability of the nucleic acid molecule to mediate alteration of gene expression by antisense or co-suppression technology. "Substantially similar" also refers to modifications of the nucleic acid molecules of the instant invention (such as deletion or insertion of one or more nucleotide bases) that do not substantially affect the functional properties of the resulting transcript vis-a-vis the ability to mediate alteration of gene expression by antisense or co-suppression technology or alteration of the functional properties of the resulting protein molecule. The invention encompasses more than the specific exemplary sequences.

For example, it is well known in the art that antisense suppression and co-suppression of gene expression may be accomplished using nucleic acid molecules representing less than the entire coding region of a gene, and by nucleic acid molecules that do not share 100% identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determining retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C.), with the sequences exemplified herein. Preferred substantially similar nucleic acid molecules of the instant invention are those nucleic acid molecules whose DNA sequences are at least 80% identical to the DNA sequence of the nucleic acid molecules reported herein. More preferred nucleic acid molecules are at least 90% identical to the DNA sequence of the nucleic acid molecules reported herein. Most preferred are nucleic acid molecules that are at least 95% identical to the DNA sequence of the nucleic acid molecules reported herein.

A "substantial portion" refers to an amino acid or nucleotide sequence which comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.* 215:403–410 (1993); see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid molecule comprising the primers. Accordingly, a "substantial portion" of a nucleotide sequence comprises enough of the sequence to afford specific identification and/or isolation of a nucleic acid molecule comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for the purpose known to those skilled in the art. Accordingly, the instant invention comprises the complete sequences as reported in the accompanying Sequence Listing, as well as substantial portions of those sequences as defined above.

The term "complementary" describes the relationship between nucleotide bases that are capable to hybridizing to one another. For example, with respect to DNA, adenosine is complementary to thymine and cytosine is complementary to guanine. Accordingly, the instant invention also includes isolated nucleic acid molecules that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data. Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG Pileup program found in the GCG program package, using the Needleman and Wunsch algorithm with their standard default values of gap creation penalty=12 and gap extension penalty=4 (Devereux et al., *Nucleic Acids Res.* 12:387–395 (1984)), BLASTP, BLASTN, and FASTA (Pearson et al, *Proc. Natl. Acad Sci. USA* 85:2444–2448 (1988). The BLASTX program is publicly available from NCBI and other sources (*BLAST Manual*, Altschul et al., Natl. Cent. Biotechnol. Inf., Natl. Library Med. (NCBI NLM) NIH, Bethesda, Md. 20894; Altschul et al., *J Mol. Biol.* 215:403–410 (1990); Altschul et al., "Gapped BLAST and PSI-BLAST: a new generation of protein database search programs", *Nucleic Acids Res.* 25:3389–3402 (1997)). Another preferred method to determine percent identity, is by the method of DNASTAR protein alignment protocol using the Jotun-Hein algorithm (Hein et al., *Methods Enzymol.* 183:626–645 (1990)). Default parameters for the Jotun-Hein method for alignments are: for multiple alignments, gap penalty=11, gap length penalty=3; for pairwise alignments ktuple=6. As an illustration, by a polynucleotide having a nucleotide sequence having at least, for example, 95% "identity" to a reference nucleotide sequence it is intended that the nucleotide sequence of the polynucteotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide. or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence is intended that the amino acid sequence of the polypeptide is identical to the reference sequence except that the polypeptide sequence may include up to five amino acid alterations per each 100 amino acids of the reference amino acid. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

The term "percent homology" refers to the extent of amino acid sequence identity between polypeptides. When a first amino acid sequence is identical to a second amino acid sequence, then the first and second amino acid sequences exhibit 100% homology. The homology between any two polypeptides is a direct function of the total number of matching amino acids at a given position in either sequence, e.g., if half of the total number of amino acids in either of the two sequences are the same then the two sequences are said to exhibit 50% homology.

"Codon degeneracy" refers to divergence in the genetic code permitting variation of the nucleotide sequence without effecting the amino acid sequence of an encoded polypeptide. Accordingly, the instant invention relates to any nucleic acid molecule that encodes all or a substantial portion of the amino acid sequence encoding the putative efflux protein as set forth in SEQ ID NO:2. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. An "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg (*Biochemistry of Plants* 15:1–82 (1989)). It is further recognized that since in most cases the exact boundaries of regulatory sequences have not been completely defined, DNA molecules of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner et al., *Mol. Biotech.* 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell* 1:671–680 (1989).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet and has an effect on cellular processes.

The term "operably linked" refers to the association of nucleic acid sequences on a single nucleic acid molecule so that the function of one is affected by the other. For example, a promoter is operably linked with a coding sequence when it affects the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid molecule of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or nontransformed organisms. "Co-suppression" refers to the production of sense RNA transcripts capable of suppressing the expression of identical or substantially similar foreign or endogenous genes (U.S. Pat. No. 5,231,020).

"Altered levels" refers to the production of gene product (s) in organisms in amounts or proportions that differ from that of normal, wild-type, or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Transformation" refers to the transfer of a nucleic acid molecule into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al., Meth. Enzymol. 143:277 (1987)) and particle-accelerated or "gene gun" transformation technology (Klein et al., *Nature, London* 327:70–73 (1987); U.S. Pat. No. 4,945,050).

The term "pobA hybridization probe" refers to a 1.2-kb PCR amplification product produced by amplification of *Pseudomonas mendocina* genomic DNA with primers based on the nucleotide sequence of the *Pseudomonas fluorescens* pobA gene (SEQ ID NO:5) as described by van Berkel et al., *Eur. J Biochem.* 210:411–419 (1992).

The term "4.5×(−) Pseudomonas" refers to a genetically manipulated *Pseudomonas mendocina* having mutations or disruptions in the putatuve efflux 4.5× gene such that the genetically manipulated *Pseudomonas mendocina* is unable to grow in the presence of chloramphenicol.

The term "efflux 4.5× gene" refers to a novel putative efflux gene which is located immediately downstream of the pobA gene in *Pseudomonas mendocina*. "Efflux protein" refers to the polypeptide that is encoded by the putative efflux 4.5× gene which is located immediately downstream of the pobA gene in *Pseudomonas mendocina*.

The term "aromatic organic substrate" refers to an aromatic compound that is degraded by the TMO enzymatic pathway. Examples of suitable aromatic substrates include, but are not limited to, toluene, p-hydroxylbenzyl alcohol, p-hydroxybenz-aldehyde and p-cresol.

The term "carbon source" refers to a substrate suitable for bacterial cell growth that is distinct from the aromatic substrate. Suitable carbon substrates include but are not limited to glucose, succinate, lactate, acetate, ethanol, monosaccharides, oligosaccharides, polysaccharides, or mixtures thereof.

The term "suicide vector" refers to a vector generally containing a foreign DNA fragment to be expressed in a suitable host cell, coupled with a genetic element that will be lethal to the host cell unless the cell is able to express the foreign DNA. "Suicide vector" is also understood to mean a non-replicating vector capable of transfecting a host cell and facilitating the incorporation of foreign DNA into the genome of the host cell. Such a vector does not replicate and is thus destroyed after incorporation of the heterologous DNA. Examples of common suicide vectors and their construction may be found in Sambrook, J., Fritsch, E. F. and Maniatis, T. *Molecular Cloning: A Laboratory Manual*; Cold Spring Harbor Laboratory Press: Cold Spring Harbor, N.Y. (1989).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, N.Y. (1989); (hereinafter "Maniatis").

One of the most significant aspects in the development of the present invention involves the potential biological function of the putative efflux 4.5× gene with both chloramphenicol and PHBA resistance. Creation of the 4.5×(−) Pseudomonas mutants preceeded by (i) the isolation of a pobA hybridization probe; (ii) isolation of the 4.5 kb gene fragment from a TMO variant using the probe; and (iii) disruption of 4.5× gene using an KamR gene cassette and subsequent cloning and expression into a suicide vector.

The nucleic acid molecules of the instant invention may be used to isolate cDNAs and genes encoding a homologous putative efflux 4.5× gene from the same or other bacterium species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction or ligase chain reaction).

For example, putative efflux 4.5× genes, either as cDNAs or genomic DNAs, could be isolated directly by using all or a portion of the instant nucleic acid molecule as DNA hybridization probes to screen libraries from any desired plant employing methodology well known to those skilled in the art. Specific oligonucleotide probes based upon the instant putative efflux 4.5× gene sequence can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid molecule may be used in polymerase chain reaction protocols to amplify longer nucleic acid molecules encoding homologous putative efflux 4.5x genes from DNA or RNA. The polymerase chain reaction may also be performed on a library of cloned nucleic acid molecules wherein the sequence of one primer is derived from the instant nucleic acid molecules, and the sequence of the other primer takes advantage of the presence of the polyadenylic acid tracts to the 3' end of the mRNA precursor encoding plant ARF. Alternatively, the second primer sequence may be based upon sequences derived from the cloning vector. For example, the skilled artisan can follow the RACE protocol (Frohman et at., *Proc. Natl. Acad. Sci., USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *Proc. Natl. Acad. Sci., USA* 86:5673 (1989); Loh et al., *Science* 243:217 (1989)). Products generated by the 3' and 5' RACE procedures can be combined to generate full-length cDNAs (Frohman et al., *Techniques* 1:165 (1989)).

Finally, availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lemer et al., *Adv. Immunol.* 36:1 (1984); Maniatis).

Overexpression of the putative efflux 4.5x gene may be accomplished by first constructing a chimeric gene in which the efflux coding region is operably linked to at least one promoter capable of directing expression of a gene in the desired tissues at the desired stage of development. For convenience, the chimeric gene may comprise promoter sequences and translation leader sequences derived from the same genes. 3' Non-coding sequences encoding transcription termination signals must also be provided. The instant chimeric gene may also comprise one or more introns in order to facilitate gene expression.

A plasmid vector comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.* 4:2411–2418 (1985); De Almeida et al., *Mol. Gen. Genetics* 218:78–86 (1989)), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the putative efflux protein to different cellular compartments or to facilitate its secretion from the cell. Therefore, the chimeric gene described above may be further supplemented by altering the coding sequences to encode the efflux protein with appropriate intracellular targeting sequences such as transit sequences (Keegstra et al., *Cell* 56:247–253 (1989)), signal sequences or sequences encoding endoplasmic reticulum localization (Chrispeels et at., *Ann. Rev. Plant Phys. Plant Mol. Biol.* 42:21–53 (1991)), or nuclear localization signals (Raikhel et al., *Plant Phys.* 100: 1627–1632 (1992)) added and/or with targeting sequences that are already present removed. While the references cited give examples of each of these, the list is not exhaustive and more targeting signals of utility may be discovered in the future.

The putative efflux protein produced in heterologous host cells, particularly in the cells of microbial hosts, can be used to prepare antibodies to the proteins by methods well known to those skilled in the art. The antibodies are useful for detecting the putative efflux protein in situ in cells or in vitro in cell extracts. Preferred heterologous host cells for production of the putative efflux protein are microbial hosts. Microbial expression systems and expression vectors containing regulatory sequences that direct high level expression of foreign proteins are well known to those skilled in the art. Any of these could be used to construct chimeric genes for production of the putative efflux protein. These chimeric genes could then be introduced into appropriate microorganisms via transformation to provide high level expression of putative efflux protein. Vectors or cassettes useful for the transformation of suitable host cells are well known in the art. Typically, the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

The instant nucleic acid molecules may be used as a restriction fragment length polymorphism (RFLP) marker. Southern blots (Maniatis) of restriction-digested plant genomic DNA may be probed with the nucleic acid molecules of the instant invention. The resulting banding patterns may then be subjected to genetic analyses using computer programs such as MapMaker (Lander et al., *Genomics* 1:174–181 (1987)) in order to construct a genetic map. In addition, the nucleic acid molecule of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al., *Am. J. Hum. Genet.* 32:314–331 (1980)).

Nucleic acid probes derived from the instant nucleic acid sequences may also be used for physical mapping (i.e., placement of sequences on physical maps; see Hoheisel et al., *Nonmammalian Genomic Analysis: A Practical Guide*, pp. 319–346, Academic Press (1996), and references cited therein).

In another embodiment, nucleic acid probes derived from the instant nucleic acid sequences may be used in direct fluorescence in situ hybridization (FISH) mapping. Although current methods of FISH mapping favor use of large clones (several to several hundred kb), improvements in sensitivity may allow performance of FISH mapping using shorter probes.

A variety of nucleic acid amplification-based methods of genetic and physical mapping may be carried out using the instant nucleic acid sequences. Examples include allele-specific amplification, polymorphism of PCR-amplified fragments (CAPS), allele-specific ligation, nucleotide extension reactions, Radiation Hybrid Mapping and Happy Mapping. For these methods, the sequence of a nucleic acid fragment is used to design and produce primer pairs for use in the amplification reaction or in primer extension reactions. The design of such primers is well known to those skilled in the art. In methods using PCR-based genetic mapping, it may be necessary to identify DNA sequence differences between the parents of the mapping cross in the region corresponding to the instant nucleic acid sequences. This, however, is generally not necessary for mapping methods. Such information may be useful in plant breeding in order to develop lines with desired phenotypes.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

GENERAL METHODS

Standard recombinant DNA and molecular cloning techniques used in the Examples are well known in the art and are described by Sambrook, J., Fritsch, E. F. and Maniatis, T. in *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist in *Experiments with Gene Fusions*, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).
Cell strain:
*Pseudomonas mendocina* KR-1 strain (U.S. Pat. No. 5,171,684 (Amgen)) was used as indicated in the following Examples.

Example 1

Isolation of Putative Efflux 4.5x Gene from *Pseudomonas mendocina* Genomic DNA

The putative efflux 4.5x gene from *Pseudomonas mendocina* was obtained during the isolation of the pobA gene from *Pseudomonas mendocina* KR-1 (U.S. Pat. No. 5,171,684 (Amgen)). PCR was first conducted for generating a DNA hybridization probe for the pobA gene. The primers used for PCR were based on the published DNA sequences of *Pseudomonas fluorescens* (van Berkel et al., Eur. J Biochem. 210:411–419 (1992)) and consisted of the following nucleotides:
Primer 1- (SEQ ID NO:5)
5' -CARTTRCTNCAYAANGTNGGNAT-3'
Primer 2- (SEQ ID NO:6)
5'-CTAYTCNATYTCYTCRTANRG-3'
Primers 1 and 2 were used in a PCR reaction consisting of 100 µL reaction mixture which contained 0.5 mM dNTPs, reaction buffer (final concentration of 10 mM Tris-HCl, pH 8.3, 50 mM KCl, 1.5 mM $MgCl_2$, and 0.01% gelatin), 0.1 µg of *Pseudomonas mendocina* genomic DNA, and 1 unit of Taq® DNA polymerase.

The DNA sample.was denatured at 94° C. for 1 min, and annealed at 45° C. for 2 min. Polymerization was done at 72° C. for 3 min with an increased extention time of 5 sec per cycle. The polymerase chain reaction was accomplished by 30 cycles. The PCR DNA fragment was detected and analyzed by regular 1% agarose gel electrophoresis with ethidium bromide. A 1.2-kb PCR DNA fragment containing the pobA gene was isolated and cloned into the vector of PCRscript (Pharmacia Biotech, Piscataway, N.J.).

50 mL of culture medium was used for the isolation of *Pseudomonas mendocina* genomic DNA. The cells of an overnight culture were spun down at 6000 rpm, 4° C. for 10 min. Supernatant was decanted and the pellets were resuspended with 5 mL TEG (25 mM Tris-HCl, 10 mM EDTA, 50 mM glucose, pH 8). About 1.5 mL of RNAse (100 µg/mL) was added into the mixture. The sample was kept at room temperature for 5 min, and then extracted with phenol twice. The two phases were separated by a centrifugation at 6000 rpm for 10 min. The aqueous phase was extracted with phenol:chloroform twice. Two volumes of 100% ethanol was added to the aqueous phase to precipitate DNA. After 20 min, the solution was centrifuged at 10,000 rpm, and the pellet was collected, dried, and resuspended in about 2 to 5 mL TE buffer (10 mM Tris-HCl, 1 mM EDTA, pH 7.6). The DNA samples were then dialyzed against TE buffer at 4° C. overnight.

10 µg of *Pseudomonas mendocina* genomic DNA was used for Southern blot analysis using the pobA hybridization probe described above. DNA samples were first digested with EcoRI, HindIII and SphI and the digests were analyzed by 1% agarose gel electrophoresis. The DNA samples were then transferred to nitrocellulose membrane by denaturation and neutralization as described previously. The membranes were exposed to ultraviolet light for about 2 min to produce nucleic acid crosslinking. The membranes were then prehybridized for about 1 to 2 h at 65° C. in a solution containing 5xSSC, 0.1% (w/v) SDS, 0.5% (w/v) blocking reagent (DuPont, Wilmington, Del.) and 5% (w/v) Dextran Sulfate.

For ease of identification, the 1.2-kb DNA pobA probe was labeled with a fluorescein nucleotide in a 30-µL reaction mixture containing a random primer, reaction buffer, fluorescein nucleotide mix and Klenow enzyme at 37° C. for 1 h. The labeled probe was then hybridized to the membrane-bound genomic DNA in the same buffer for 16 h at 65° C.

After hybridization, the membrane was washed for 15 min in 2xSSC, 0.1% SDS, followed by a second 15 min wash in 0.2xSSC, 0.1% SDS at 65° C. The membrane was then blocked for 1 h in buffer containing 0.5% blocking reagent and then incubated with antifluoresein HRP conjugate (1:1000) at room temperature for 1 h.

After the incubation, the membranes were washed four times for 5 min with 0.1M Tris-HCl pH 7.5, 0.15 M NaCl, and incubated in a chemiluminescence reagent (Renaissance, nucleic acid chemiluminescent reagent, DuPont, Wilmington, Del.) for 1 min at room temperature, and then exposed to the REFLECTION™ film (DuPont, Wilmington, Del.). In this manner 4.5-kb portions of the genomic DNA hybridizing to the pobA probe were isolated.

Example 2

Cloning and Identification of *Pseudomonas mendocina* Putative Efflux 4.5x Gene

The 4.5-kb portions of wildtype *Pseudomonas mendocina* KR-1 DNA generated as described in Example 1 were used to construct a genomic DNA library as follows. Genomic DNA was restricted with SphI and 4.5-kb restriction fragments were isolated and recovered from an agarose gel using a DNA preparation kit (GeneClean Bio101,Vista, Calif.). Isolated DNA was then ligated into pUC19 at the appropriate SphI restriction site and used to transform *Escherichia coli* DH5α. Minipreparation and miniagarose gel electrophoresis indicated that about 80% of the transformants contained an insert of about 4.5 kb in length.

The positive transformants were first grown on the LB agar plates overnight. The plates were chilled to 4° C. for 1 h. The colonies were then transferred onto the membrane discs. The membrane discs were treated twice with 0.5N NaOH for 2-min, and then washed twice for 2-min with 1M Tris-HCl, pH 7.5. The DNA was fixed on the membrane by ultraviolet crosslinking. Membranes were prehybridized for about 1 to 2 h at 65° C. in a solution containing 5×SSC, 0.1% (w/v) SDS, 0.5% (w/v) blocking reagent (DuPont, Wilmington, Del.) and 5% (w/v) Dextran Sulfate.

The 1.2-kb DNA fragment of the pobA gene, constituting the pobA hybridization probe, was labeled and used to detect the presence of the 4.5x gene in essentially the same manner as it was used to confirm the presence of the pobA gene as described in Example 1.

The plasmid DNA was isolated from the positive colony detected with colony hybridization. The size of the insert was determined by SphI digestion and miniagarose gel electrophoresis. The plasmid containing the 4.5x gene was used for DNA sequencing. DNA sequencing with synthetic primers was done at The Biopolymer Laboratory, Department of Microbiology and Immunology at the University of Maryland School of Medicine according to standard methods. Accordingly the sequence of the 4.5x gene was determined and is given as SEQ ID NO:1.

The generated gene sequence was identified by conducting a BLAST (Basic Local Alignment Search Tool; Altschul et al., *J Mol. Biol.* 215:403–410 (1993); see also www.ncbi.nlm.nih.gov/BLAST/) search for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL, and DDBJ databases). The 4.5x DNA sequence obtained was analyzed using the BLASTN algorithm provided by the National Center for Biotechnology Information (NCBI). In addition, the DNA sequence was translated in all reading frames and compared for similarity to all publicly available protein sequences contained in the "nr" database using the BLASTX algorithm (Gish et al., *Nature Genetics* 3:266–272 (1993)) provided by the NCBI. For convenience, the expected value of observing a match of a cDNA sequence to a sequence contained in the searched databases merely by chance as calculated by BLAST are reported herein as "E" values. The E value estimates the statistical significance of the match, specifying the number of matches with a given score, that are expected in a search of a database of this size absolutely by chance.

The BLAST search using the putative 4.5x gene (SEQ ID NO:1) showed no significant sequence similarity to any known DNA sequence in the database. The BLASTX search revealed relatively low similarity to the sequences set out in Table 1 below. The translated amino acid sequence of the putative efflux 4.5x gene is shown in SEQ ID NO:2. Sequence alignments, BLAST scores and probabilities indicate that the instant nucleic acid molecule encodes for an efflux protein. The amino acid sequence of the instant putative efflux protein shows approximately 20% sequence identity to the *Bacillus subtilis* protein, approximately 32% sequence identity to the *Streptomyces lividans* protein, and approximately 32% sequence identity to the *Escherichia coli* protein. A number of highly conserved regions or motifs were identified within the amino acid sequence of the putative efflux 4.5x gene. In particular, the motifs which are conserved throughout the Major Facilitator Superfamily were also found in N-terminal region of the 4.5x protein.

TABLE 1

BLAST Search Results[a]

| gi identifier (sequence ID)[b] | Description[c] | Reference[d] | E value[e] |
|---|---|---|---|
| 3116222 | Arthrobacter sp. transporter protein | Nishiya, Y. and T. Imanaka. 1993. Cloning and sequencing of the sarcosine oxidase gene from Arthrobacter sp. TE1826. J. Ferment. Bioeng. 75:239–244. | 3e-16 |
| 3257679 | *Pyrococcus horikoshii* 372aa long hypothetical protein | Kawarabayasi, Y et al. 1998. Complete Sequence and Gene Organization of the Genome of a Hyper-thermophilic Archaebacterium, *Pyrococcus horikoshii* OT3. DNA Research 5:55–76. | 2e-14 |
| 1706916 | *Escherichia coli* fosmidomycin resistance protein, Fsr | Fujisaki, S. et al. 1996. Cloning of a gene from *Escherichia coli* that confers resistance to fosmidomycin as a consequence of amplification. Gene 175:83–87. | 9e-013 |
| 1842056 | *Acinetobacter calcoaceticus* ADP1 cis,cis-muconate transport protein MucK | Williams, P. A. and Shaw, L. E. 1997. mucK, a gene in *Acinetobacter calcoaceticus* ADP1 (BD413), encodes the ability to grow on exogenous cis,cis-muconate as the sole carbon source. J. Bacteriol. 179:5935–5942. | 2e-09 |
| 732369 | *Bacillus subtilis* hypothetical 44.5 KD transmembrane protein | Glaser, P. et al. 1993. *Bacillus subtilis* genome project: cloning and sequencing of the 97-kb region from 325 degrees to 333 degrees. Mol. Microbiol. 10:371–384. | 2e-08 |
| 399267 | *Streptomyces lividans* chloramphenicol resistance protein | Dittrich, W. et al. 1991. An amplifiable and deletable chloramphenicol-resistance determinant of *Streptomyces lividans* 1326 encodes a putative transmembrane protein. Mol. Microbiol. 5:2789–2797. | 4e-08 |
| 2791591 | *Mycobacterium tuberculosis* hypothetical protein Rv2994 (similar to fluoroquinolone efflux proteins of Staphylococci) | Cole, S. T. et al. 1998. Deciphering the biology of Mycobacterium tuberculosis from the complete genome sequence. Nature 393:537–544. | 1e-07 |
| 1945096 | *Streptomyces lividans* chloramphenicol resistance protein | Sadaie, Y. et al. 1996. Direct Submission | 1e-07 |
| 731351 | *Bacillus subtilis* hypothetical 44.9 KD transmembrane protein | Cosmina, P., et al. 1993. Sequence and analysis of the genetic locus responsible for surfactin synthesis in *Bacillus subtilis*. Mol. Microbiol. 8:821–831. | 2e-07 |

TABLE 1-continued

BLAST Search Results[a]

| gi identifier (sequence ID)[b] | Description[c] | Reference[d] | E value[e] |
|---|---|---|---|
| 2271501 | Acinetobacter calcoaceticus ADP1 putative transport protein | Segura, A. and Ornston, N. L. 1997. pZR135: vanillate demethylase region in Acinetobacter. Unpublished | 2e-07 |

[a]A BLAST search using blastp 2.0.6 (comparison of an amino acid query sequence against a protein sequence database) was performed using the 416 amino acid sequence of the putative 4.5X protein as the query sequence against the protein database [Non-redundant GenBank CDS translations + PDB (Brookhaven Protein Data Bank) + SwissProt + SPupdate + PIR; 332,170 sequences; 101,325,347 total letters]. The search was conducted without the default filter and with the '-gi' option for BLAST output checked.
[b]These numbers are assigned by the National Center for Biotechnology Information (NCBI) for all sequences contained within NCBI's sequence databases and were part of the BLAST output. They may be used in ENTREZ protein sequence searches under the search field of 'sequence ID.'
[c]Definition lines present as part of the BLAST output or the sequence record. They serve to define and describe the corresponding sequence.
[d]Represent 'Reference 1' cited in each sequence record.
[e]Expect value. The Expect value estimates the statistical significance of the match, specifying the number of matches, with a given score, that are expected in a search of a database of this size absolutely by chance.

Example 2.5

Subsequent sequence analysis of SEQ ID NO:2 determined that no stop codon existed. Therefore, Applicant concluded an incomplete open reading frame existed.

Subsequent Southern hybridization revealed that a NotI digestion chromosomal DNA would yield a DNA fragment containing the full open reading frame (gene). In the manner of Example 2, restrict the genomic DNA with NotI instead of SPH1 to obtain the full open reading frame.

Example 3

Figure 1:
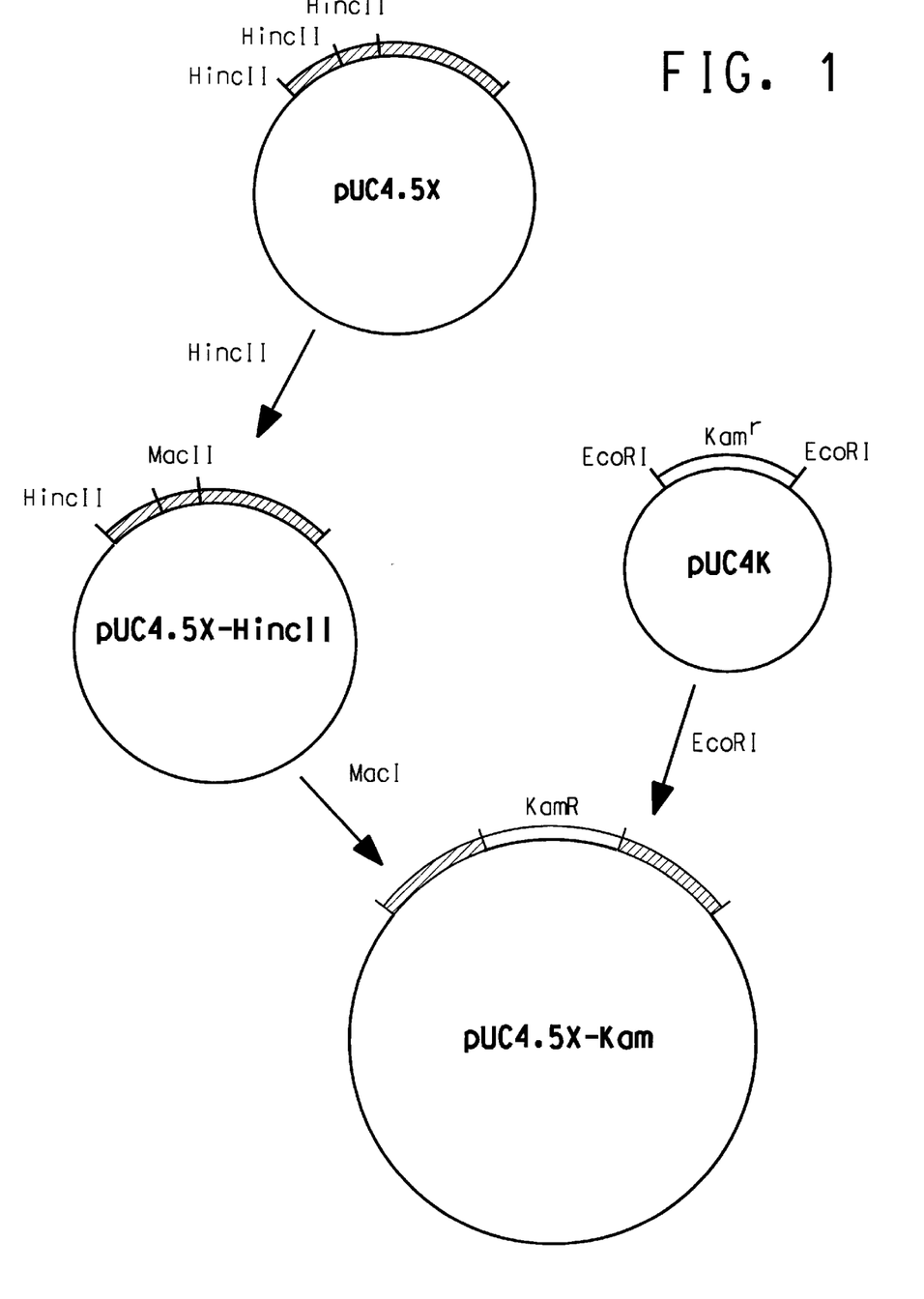
FIG. 1 schematically represents plasmid vectors used for the disruption of the putative efflux 4.5x gene in *Pseudomonas mendocina*.

Disruption of the Putative Efflux 4.5× Gene by Deletion and then Insertion into a Suicide Vector The Kam resistance gene cassette was removed from the plasmid pUC4K (Pharmacia Biotech, Piscataway, N.J.) by digesting with EcoRI (FIG. 1). Sticky ends were then repaired with Klenow. The pUC4.5× plasmid, containing the 4.5-kb fragment, was then digested with HincII, which resulted in a HincII fragment being deleted from the 4.5-kb SphI fragment (FIG. 1). The resulting plasmid pUC4.5×-HincII was digested with MscI. The Kam resistance gene cassette was then inserted into the MscI-digested pUC4.5×-HincII plasmid to form the plasmid of pUC4.5×-Kam. The orientation of the Kam gene cassette in the pobA gene was determined by the restriction mapping of the resulted plasmid.

The disrupted 4.5× gene with the Kam gene cassette was digested with SphI and the resulting DNA fragment was ligated with the SphI digested pARO180 plasmid to produce pARO4.5×-K, which was then used to transform S17-1 Escherichia coli (Parke, Gene, 93:135–137 (1990)). Positive colonies were selected on the agar plates on the basis of Kam resistance.

Construction of suicide vectors are common and well known in the art and have been developed to transfect a variety of microorganisms to facilitate genetic manipulations. For example, suicide vectors capable of transfecting Salmonella (Galen et al., 96th General Meeting of the American Society for Microbiology, New Orleans, La., USA, May 19–23, 1996. Abstracts of the General Meeting of the American Society for Microbiology 96:529 (1996)), Streptococcus (Brooker et al., Lett. Appl. Microbiol. 21:292–297 (1995)), Rhizobium (Safronova et al., Genetika 30:763–768 (1994)), Rhodobacter (Penfold et al., Gene (Amsterdam) 118:145–146 (1992)) and other Gram-negative bacteria (Skrzypek et al., Plasmid 29:160–163 (1993)), have all been constructed. Suicide vectors will be constructed so as to accommodate the specific host to be transfected and to accomplish the desired purpose. Generally suicide vectors useful in the present invention are non-replicating and capable of transfecting a host cell with foreign DNA and facilitating incorporation of that DNA into the genome of the host cell. Such vectors are destroyed after transfecting the desired host with foreign DNA.

Within the context of the present invention, a mobilizing, narrow host range vector, which will replicate to high copy number in Escherichia coli is preferred. Such vectors will be able to be efficiently transferred to other Gram-negative bacteria from a mobilizing host strain such as Escherichia coli S17-1 (Parke et al., supra). For the purposes of the present invention a variety of suicide vectors will serve to carry the disrupted 4.5× gene for transfection into a suitable host where pARO 180 is preferred.

The process of gene disruption analysis is common and well known in the art. Gene disruption involves inserting a non-coding DNA fragment or a DNA fragment of a selectable marker in the coding region of a target structural gene and transforming a host containing an endogenous target gene with that disrupted construct. Homologous recombination between the disrupted gene and the endogenous gene will result in inactivation of the endogenous gene in the host organism. Gene disruption is used in a variety of organisms such as Mycobacterium (Balasubramanian et al., J Bacteriol. 178:273–279 (1996)), Saccharomyces (Daran et al., Eur. J of Biochem. 233:520–530 (1995)), Brevibacterium (Su Y-C et al., Proceedings of the National Science Council Republic of China Part B, Life Sciences 19:113–122 (1995)), as well as Escherichia coli (Cherepanov et al., Gene (Amsterdam) 158:9–14 (1995)).

To transfer the plasmid containing the disrupted 4.5× gene to Pseudomonas mendocina KR-1, a single colony of Escherichia coli strain S17–1 having the plasmid of pARP4.5×-Kam was inoculated in 20 mL LB medium, and grown at 37° C. to log phase. Another colony of Pseudomonas mendocina KR-1 was inoculated in 20 mL LB medium and incubated at 30° C. and grown to log phase.

The cells of both cultures were washed twice with LB medium and resuspended in LB medium. Escherichia coli strain S17-1 cells and Pseudomonas mendocina KR-1 were mixed in a ratio of 1:4 and were plated on agar plates of LB medium. The plates were incubated at 30° C. for 8 h. The cells were collected and then plated on the agar plates containing phosphate buffer, 1 mM succinate, 25 μg/mL Kanamycin, and Kam-resistant colonies were selected.

Positive transformants were selected on the basis of antibiotic resistance and the presence of the disrupted 4.5× gene was confirmed by PCR. This process is called transformation by conjugation. Alternatively, cells may be transformed by known procedures such as by protocols involving calcium-permeabilized cells, electroporation, or by transfection using a recombinant phage virus (Maniatis).

The disrupted 4.5× gene is an integrating DNA fragment which has a DNA sequence homology to a target site in the genome of the host cell so that the chimerical DNA fragment of 4.5× gene and a drug-resistance gene can be integrated into the genome of the host *Pseudomonas mendocina*.

The transformed *Pseudomonas mendocina* KR-1, carrying the disrupted putative efflux 4.5× gene, was grown on the agar plates in the presence of different antibiotics or high concentration of PHBA. The growth of the strain with the disrupted 4.5× gene was compared with that of wild type *Pseudomonas mendocina* strain KR-1. The strain with disrupted 4.5× gene was unable to grow on the plates with chloramphenicol concentration ranging from 5 $\mu$g/mL to 25 $\mu$g/mL while the same strain showed similar growth as wildtype strain on the plates with ampicillin. The growth of 4.5×(−) strain in the presence of 50 mM PHBA was four times slower than that of the wildtype strain under the same condition.

The primers 5'-ATGCTCAGTAGAGTCGGGTGGCT GCA -3' (SEQ ID NO:3) and 5'-TTACGCCAAGCTTGC ATGCCGCCG -3' (SEQ ID NO:4), based on the sequence of the putative efflux 4.5× gene from *Pseudomonas mendocina* KR-1 (SEQ ID NO:1) were used in a PCR reaction consisting of 50 $\mu$L reaction mixture which contained 0.2 mM each dNTPs, reaction buffer of 10 $\mu$l Buffer B (final concentration of 60 mM Tris-SO$_4$, pH 9.1), 18 mM (NH$_4$)$_2$SO$_4$, 2 mM MgSO$_4$, 0.1 $\mu$g of *Pseudomonas mendocina* genomic DNA, and 2 $\mu$L of ELONGase® Enzyme.

The DNA sample was pre-denatured at 94° C. for 1 min, denatured for 30 sec and annealed at 55° C. for 30 seconds. Polymerization was done at 68° C. for 5 min with an increased extension time of 5 sec per cycle. The polymerase chain reaction was accomplished by 35 cycles. The PCR DNA fragment was detected and analyzed by regular 1% agarose gel electrophoresis with ethidium bromide.

Example 4

Antibiotic Resistance and Cell Tolerance to PHBA in Wildtype and 4.5×(−) *Pseudomonas mendocina*

The colonies were inoculated on the LB plates with different antibiotics separately. The antibiotics include Amp (50 $\mu$g/mL), Strep (10 $\mu$g/mL), Tec (10 $\mu$g/mL), Kam (25 $\mu$g/mL) and CM (5 $\mu$g/mL, 15 $\mu$g/mL and 25 $\mu$g/mL). The plates were kept at 30° C. for 48 hour. The growth of the colonies was scored based on the growth of wildtype strain KR-1 and the growth of these colonies on LB plates. Results are shown in Table 2.

TABLE 2

| | Antibiotic Resistance | |
|---|---|---|
| STRAIN | Wildtype KR-1 | 4.5X(−) Pseudomonas |
| LB | + | + |
| Amp (100 $\mu$g/mL) | + | + |

TABLE 2-continued

| | Antibiotic Resistance | |
|---|---|---|
| STRAIN | Wildtype KR-1 | 4.5X(−) Pseudomonas |
| Kam (50 $\mu$g/mL) | − | + |
| Tec (10 $\mu$g/mL) | − | − |
| CM (5 $\mu$g/mL) | + | − |
| (10 $\mu$g/mL) | + | − |
| (25 $\mu$g/mL) | + | − |

The cells were innoculated in the liquid medium consisting of minimal medium (in 1 L solution, sodium phosphate, monobasic, 1.85 g; potassium phosphate, dibasic, 5.84 g; ammonia sulphate, 1.5 g; yeast extract, 500 mg; 1× minerals, 2% glucose and 50 mM PHBA). The cultures were kept at 30° C. in a shaker incubator for 48 hours. The cell growth was monitored by optical density (O.D.) measurements using a spectrophotometer. Results are shown in Table 3. The data in Example 4 suggest that the gene is relevant to transport in the efflux system. Table 4 shows a predicted transmembrane protein topology.

TABLE 3

Sensitivity to PHBA

| | |
|---|---|
| Cell Density (O.D., 600 nm): | KR-1: 3.06  4.5X(−): 0.78 |
| Conditions: | 10 mL minimal medium with yeast extract, 50 mM PHBA, 30° C. for 24 hr |

TABLE 4

TM (transmembrane) Prediction
(Generated by ULrec3.unil.ch/software/TMPRED_form.html;
29 October 1997)

| # of transmembrance helice | from amino acid number | to amino acid number | length of transmembrane helice | score | orientation |
|---|---|---|---|---|---|
| 1 | 66 | 88 | (23) | 2184 | i-o |
| 2 | 108 | 127 | (20) | 1636 | o-i |
| 3 | 135 | 153 | (19) | 2002 | i-o |
| 4 | 157 | 175 | (19) | 1871 | o-i |
| 5 | 192 | 217 | (26) | 1335 | i-o |
| 6 | 223 | 243 | (21) | 2906 | o-i |
| 7 | 227 | 295 | (19) | 2013 | i-o |
| 8 | 317 | 335 | (19) | 2547 | o-i |
| 9 | 343 | 361 | (19) | 2182 | i-o |
| 10 | 369 | 387 | (19) | 1919 | o-i |
| 11 | 393 | 416 | (24) | 1285 | i-o |

Legend:
N-terminus inside; 11 strong transmembrane helices;
I = intra-cytoplasmic; o = extra-cytoplasmic

What is claimed is:

1. An isolated efflux protein polypeptide encoded by the isolated Pseudomonas nucleic acid molecule selected from the group consisting of:
   (a) an isolated nucleic acid molecule encoding the amino acid sequence set forth in SEQ ID NO:2;
   (b) an isolated nucleic acid molecule that hybridizes with complement of the isolated nucleic acid molecule of (a) under the following hybridization conditions: 0.1×SSC, 0.1% SDS at 65° C. and washed with 2×SSC, 0.1% SDS followed by a second wash in 0.2×SSC, 0.1% SDS.

2. The isolated polypeptide of claim 1 wherein the amino acid sequence is set forth in SEQ ID NO:2.

* * * * *